(12) United States Patent
Lee et al.

(10) Patent No.: US 7,880,138 B2
(45) Date of Patent: Feb. 1, 2011

(54) APPARATUS AND METHOD FOR ANALYZING CONTAMINANTS ON WAFER

(75) Inventors: Jae-Seok Lee, Gyeonggi-do (KR); Heung-Bin Lim, Gyeonggi-do (KR); Won-Kyung Ryu, Seoul (KR); Seung-Ki Chae, Seoul (KR); Yang-Koo Lee, Gyeonggi-do (KR); Hun-Jung Yi, Gyeonggi-do (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 419 days.

(21) Appl. No.: 11/963,662

(22) Filed: Dec. 21, 2007

(65) Prior Publication Data

US 2008/0149827 A1 Jun. 26, 2008

(30) Foreign Application Priority Data

Dec. 22, 2006 (KR) ...................... 10-2006-0132919

(51) Int. Cl.
*H01J 49/26* (2006.01)
*G01N 21/00* (2006.01)

(52) U.S. Cl. ................................... 250/288; 356/237.1

(58) Field of Classification Search ................ 250/288, 250/548; 219/121.84; 359/368
See application file for complete search history.

(56) References Cited

U.S. PATENT DOCUMENTS

| | | | | |
|---|---|---|---|---|
| 5,814,156 A | * | 9/1998 | Elliott et al. | ................... 134/1 |
| 5,958,268 A | * | 9/1999 | Engelsberg et al. | .... 219/121.84 |
| 7,312,919 B2 | * | 12/2007 | Overbeck | ................... 359/368 |
| 2002/0113218 A1 | * | 8/2002 | Okumura et al. | ............ 250/548 |

FOREIGN PATENT DOCUMENTS

| | | |
|---|---|---|
| JP | 07-159299 | 6/1995 |
| JP | 2003-098051 | 4/2003 |
| KR | 10-0244922 | 11/1999 |
| KR | 2003-0054730 | 7/2003 |
| KR | 2004-0098959 | 11/2004 |

OTHER PUBLICATIONS

English language abstract of Japanese Publication No. 07-159299.
English language abstract of Japanese Publication No. 2003-098051.
English language abstract of Korean Publication No. 10-0244922.
English language abstract of Korean Publication No. 2003-0054730.
English language abstract of Korean Publication No. 2004-0098959.

* cited by examiner

*Primary Examiner*—Nikita Wells
*Assistant Examiner*—Johnnie L Smith
(74) *Attorney, Agent, or Firm*—Volentine & Whitt, PLLC (57) ABSTRACT

Provided is an apparatus and method for analyzing contaminants on a wafer. The apparatus includes: a wafer holder for supporting a wafer on which contaminants to be analyzed are located, a laser ablation device for irradiating a laser to the wafer to extract a discrete specimen from the wafer, an analysis cell for collecting a discrete specimen from the surface of the wafer by irradiating the laser, and an analysis device connected to the analysis cell for analyzing contaminants from the collected discrete specimen.

20 Claims, 9 Drawing Sheets

APPARATUS AND METHOD FOR ANALYZING CONTAMINANTS ON WAFER

CROSS-REFERENCE TO RELATED APPLICATION

This application claims the benefit of Korean Patent Application No. 2006-132919, filed Dec. 22, 2006, the disclosure of which is hereby incorporated herein by reference in its entirety.

BACKGROUND OF THE INVENTION

1. Field of the Invention

The present invention relates to an apparatus and method for analyzing contaminants on a wafer surface, and more particularly, to an apparatus and method capable of collecting a sample of contaminants from a wafer surface and analyzing the contaminants.

2. Description of the Related Art

In recent times, high integration and compact size of a semiconductor device have been causing increased adsorption of various contaminants, especially metal contaminants generated from a semiconductor manufacturing line and during a semiconductor manufacturing process onto a wafer surface, adversely affecting performance and yield of the semiconductor device.

Therefore, a process of analyzing contaminants on a wafer surface has become essential in the manufacture of a semiconductor device.

In conventional art, analysis of contaminants has been performed by selecting a predetermined wafer between semiconductor manufacturing lines or semiconductor manufacturing processes, scanning a surface of the selected wafer using a scanning solution such as hydrogen fluoride (HF) to collect a sample for analyzing contaminants from the wafer surface, and analyzing the collected sample through a destructive analysis method using methods such as an atomic absorption spectroscopy, inductively coupled plasma mass spectroscopy (ICP-MS) etc., or a nondestructive analysis method using a total X-ray fluorescent analyzer.

However, while these methods are appropriate to analyze contaminants on a wafer surface, since it is time-consuming to collect a sample for analyzing contaminants, the entire process may be delayed. Therefore, methods of using a laser have been proposed in order to more rapidly analyze contaminants.

For example, Korean Patent Registration No. 244922, entitled "Method of Analyzing Metal Alloy as Metal Target in Semiconductor Process," registered on Nov. 24, 1999, discloses a method of analyzing contaminants contained in a metal alloy used as a metal target in a sputtering process among semiconductor processes, which may also be applied to a method of analyzing contaminants on a wafer.

Specifically, the contaminant analysis method disclosed in the above patent includes a sample cutting step of cutting a portion of a metal alloy, a surface treatment step of grinding and polishing a surface of the cut sample, a step of sputtering the surface treated sample using a laser ablation device integrated with a mass analyzer, and a step of detecting desired metal elements among metal elements separated during the sputtering step. As a result, it is possible to irradiate a laser to the cut and surface treated sample, extract a specimen for analyzing contaminants from the sample, and rapidly analyzing contaminants of the metal alloy from the extracted specimen.

A method of analyzing contaminants on a wafer adapting the impurity analysis method includes making a sample by cutting a portion of a wafer to be analyzed, moving the sample to a predetermined sealed space to irradiate a laser to the sample, and analyzing a specimen extracted from the sample to analyze contaminants on the wafer. Eventually, in the case of the conventional wafer contaminant analysis method, it is possible to irradiate the laser to the cut sample, extract contaminants from the sample of the specimen, and rapidly analyze contaminants on the wafer from the extracted sample of the specimen.

However, since the method analyzes contaminants from the sample after making the sample for analyzing contaminants on a wafer, sample making time is an additional necessity.

In addition, since the method makes the specimen by cutting the portion of the wafer before analyzing contamination of thie wafer, additional contamination may be generated during the process. That is, according to the conventional wafer contaminant analysis method, since additional contamination may be generated during the process of cutting the portion of the wafer to make the sample, data finally detected and analyzed from may be different from actual contamination of the wafer.

SUMMARY OF THE INVENTION

An embodiment of the invention provides an apparatus and method capable of detecting and analyzing contaminants on a wafer, and analyzing contaminants at a wafer level using a laser.

In one aspect, an apparatus for analyzing contaminants on a wafer is provided. The apparatus can comprise a wafer holder for supporting a wafer on which contaminants to be analyzed are located, a laser ablation device for irradiating a laser to the wafer to extract a discrete specimen from the wafer, an analysis cell for collecting a discrete specimen from the surface of the wafer by irradiating the laser, and an analysis device connected to the analysis cell for analyzing contaminants from the collected discrete specimen.

In another embodiment, the wafer holder can comprise a plate on which the wafer is mounted. The plate may have a plurality of vacuum holes for applying a vacuum to the wafer to hold the wafer in place. The apparatus may also have vacuum holes which are disposed in a radial array extending from the center of the plate.

In still another embodiment, the wafer holder can comprise a plate, a wafer support block connected to the plate to support a center portion of the wafer, and a plurality of fitting bars connected to the plate to support an edge part of the wafer. Moreover, the wafer support block and the plurality of fitting bars may include vacuum holes for applying a vacuum to the wafer. In addition, each of the fitting bars can have a side support portion for supporting a side surface of the wafer when the wafer is mounted on the fitting bars. Further, the fitting bars can be connected with respect to the wafer support block such that the fitting bars can move toward or away from the wafer support block.

In yet another embodiment, the laser ablation device may comprise a laser irradiation unit for irradiating a laser having certain intensity and characteristics to the wafer, an optical system for guiding the laser irradiated from the laser irradiation unit to the discrete specimen, and a monitoring unit for monitoring the specimen collection. Furthermore, the laser ablation device can also comprise a laser control unit connected to the laser irradiation unit, the optical system, and the monitoring unit, for adjusting the number, intensity, and characteristics of the laser irradiated for collecting the discrete specimen. The apparatus can also comprise a specimen conveyance device connected to the analysis cell for supplying a carrier gas into the analysis cell to convey the specimen collected from the wafer to the analysis device.

In yet another embodiment, the analysis cell may include a hollow cell body in contact with the wafer defining an opening for collecting the discrete specimen, a window installed at an upper part of the cell body through which a laser transmits into the cell body, a gas inlet part installed at one lower side of the cell body and supplying a carrier gas into the cell body, and a gas discharge part installed at another upper part of the cell body and conveying the specimen collected in the cell body by the carrier gas to the analysis device. Moreover, the gas inlet part can be formed of a plurality of gas inlet pipes, and the gas discharge portion is formed of at least one gas discharge pipe. In addition, the analysis cell can further comprise a sealing portion connected to a bottom surface of the cell body to isolate the interior of the cell body from the exterior.

In another embodiment the apparatus can further comprise a moving device engaged in communication with the wafer holder and the analysis cell for separately or simultaneously conveying the wafer holder and the analysis cell to adjust the location for collecting the discrete specimen. The moving device can comprise a holder moving unit engaged with the wafer holder and moving the wafer holder in a plurality of directions (such as in X, Y and/or Z directions), a cell moving unit engaged with the analysis cell and moving the analysis cell in a plurality of directions (such as in X, Y and/or Z directions), and a scan unit connected to the holder moving unit and the cell moving unit for simultaneously moving the wafer holder and the analysis cell.

In yet another embodiment, the analysis device can comprise a high-resolution inductively coupled plasma mass spectroscopy (HR-ICP-MS).

In another aspect, the invention is directed to a method of analyzing contaminants on a wafer. The method can comprise loading a wafer for analyzing contaminants on a wafer holder, isolating a specimen collection area of the entire surface of the wafer using an analysis cell, irradiating a laser to the specimen collection area to collect a specimen from the wafer, and analyzing contaminants from the collected specimen.

In another embodiment, the method may further include supplying a carrier gas into the analysis cell using a specimen conveyance device connected to the analysis cell such that the collected specimen is conveyed from the interior of the analysis cell to the analysis device. In still another embodiment, the method may further include separately moving the wafer holder and the analysis cell using a moving device engaged with the wafer holder and the analysis cell to adjust the specimen collection area. In yet another embodiment, the method may further include simultaneously moving the wafer holder and the analysis cell using a moving device engaged with the wafer holder and the analysis cell to adjust the specimen collection area.

BRIEF DESCRIPTION OF THE DRAWINGS

The foregoing and other objects, features and advantages of the invention will be apparent from the more particular description of exemplary embodiments of the present invention, as illustrated in the accompanying drawings. The drawings are not necessarily to scale, emphasis instead being placed upon illustrating the principles of the invention.

DETAILED DESCRIPTION OF THE INVENTION

The present invention will now be described more fully hereinafter with reference to the accompanying drawings, in which exemplary embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. Like numbers refer to like elements throughout the specification.

Referring to FIGS. 1 to 6, an apparatus 100 for analyzing contaminants on a wafer in accordance with an exemplary embodiment of the present invention includes a wafer holder 160 for holding a wafer W on which contaminants to be analyzed exist, a laser ablation device 110 for irradiating a laser L to the wafer W to extract a specimen from the wafer W, an analysis cell 170 for locally isolating a specimen collection area from the entire surface of the wafer W by irradiating the laser L, an analysis device 190 connected to the analysis cell 170, the analysis device 190 for analyzing contaminants from the collected specimen, a specimen conveyance device for supplying a carrier gas into the analysis cell 170 to convey the collected specimen to the analysis device 190, and a moving device 150 for separately or simultaneously conveying the wafer holder 160 and the analysis cell 170 to adjust the specimen collection area.

Figure 1:
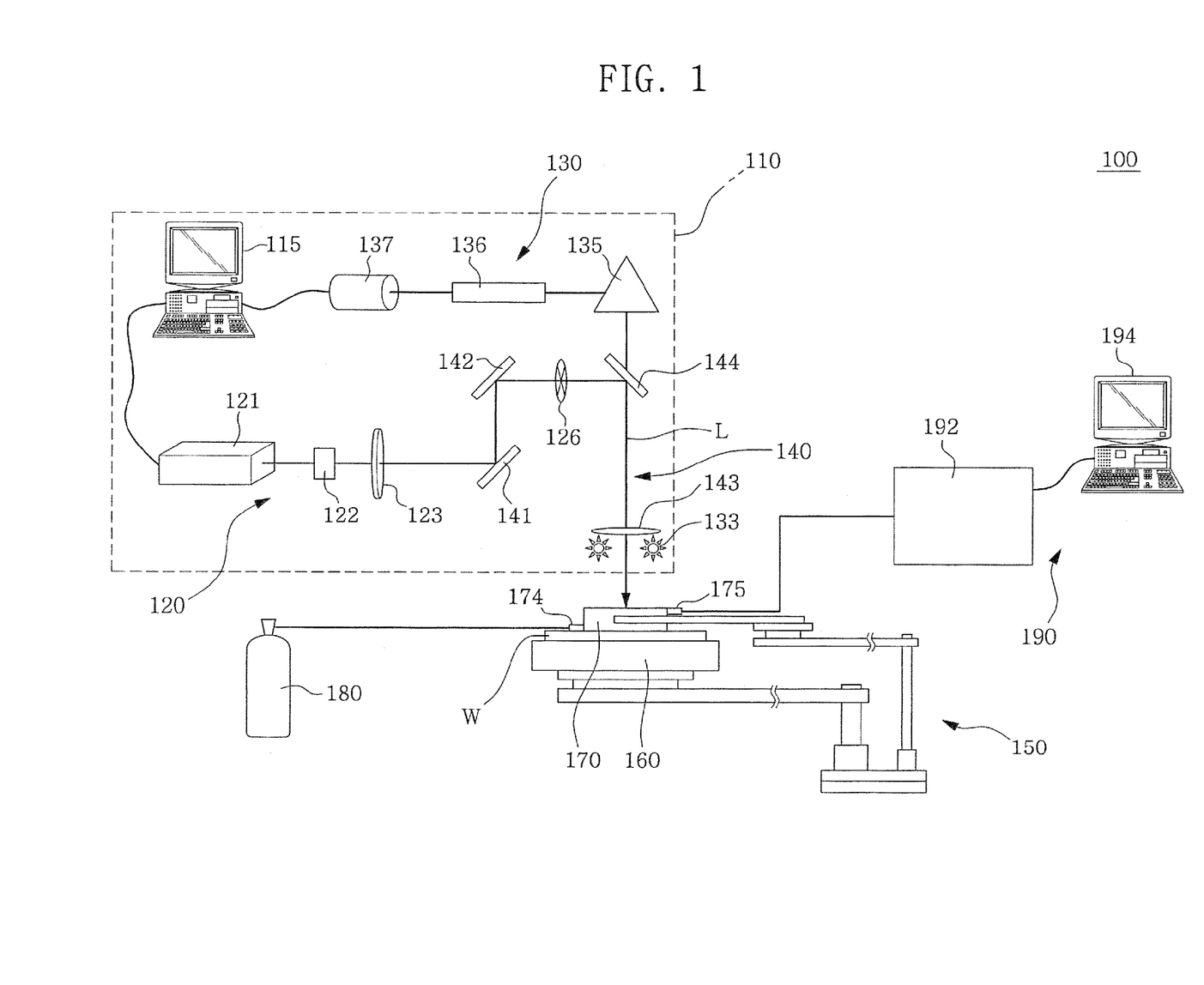
FIG. 1 is a schematic view of an apparatus for analyzing contaminants on a wafer in accordance with an exemplary embodiment of the present invention.
Figure 2:
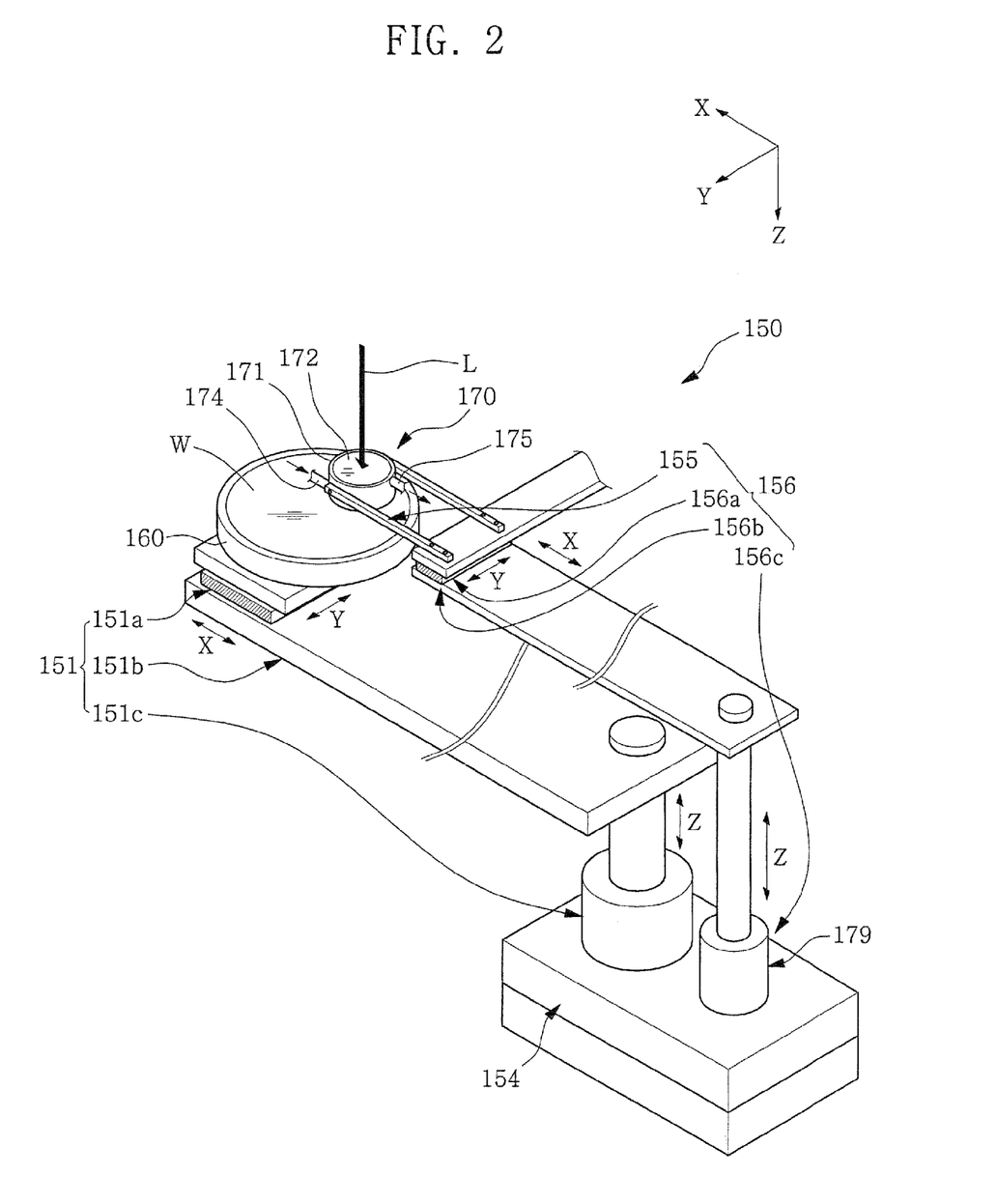
FIG. 2 is a perspective view of a wafer holder, an analysis cell, and a moving device for moving the wafer holder and the analysis cell shown in FIG. 1.
Figure 3:
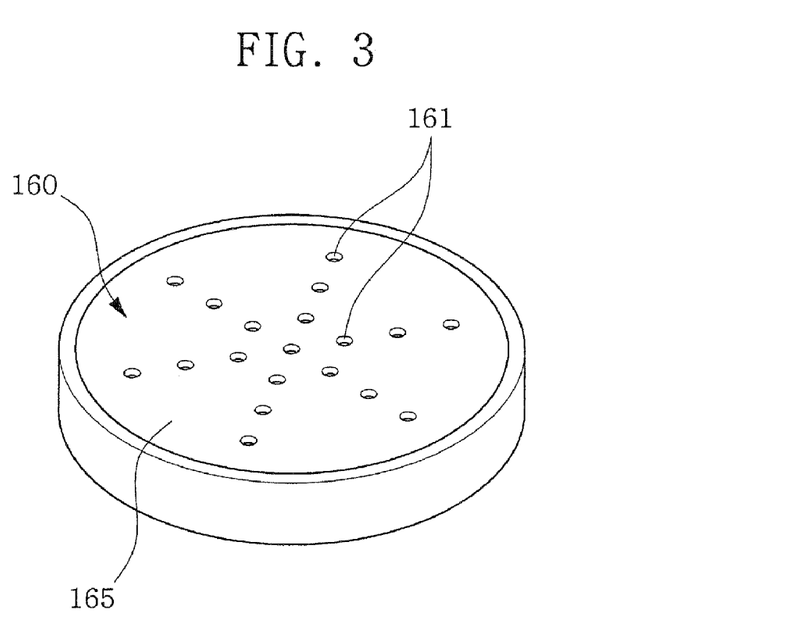
FIG. 3 is a perspective view of the wafer holder shown in FIG. 2.

Specifically, the wafer holder 160 applies vacuum to the wafer W to hold the wafer W in place when the wafer W is loaded on the wafer holder 160. Loading the wafer W may be manually performed by an operator, or automatically performed by a wafer conveyance robot (not shown).

Specifically, as shown in FIG. 3, the wafer holder 160 includes a plate 165 having a flat surface on which the wafer W is mounted. Therefore, the wafer W is loaded on an upper surface of the plate 165. The plate 165 has a plurality of vacuum holes 161 for applying a vacuum pressure to hold in place the wafer W loaded on the plate 165. Therefore, the wafer W loaded on the upper surface of the plate 165 is held on the upper surface of the plate 165 by a vacuum pressure applied through the vacuum hole 161. At this time, the vacuum pressure applied through the vacuum hole 161 may be the vacuum pressure widely used in a semiconductor manufacturing line. In this case, a vacuum supply line (not shown) generally installed in a semiconductor manufacturing line may be connected to the vacuum hole 161 to apply the vacuum pressure. In addition, the vacuum holes 161 formed in the plate 165 may be disposed in a radial manner from the center of the plate 165. In this case, the vacuum pressure can be more evenly applied onto the wafer W.

Figure 4:
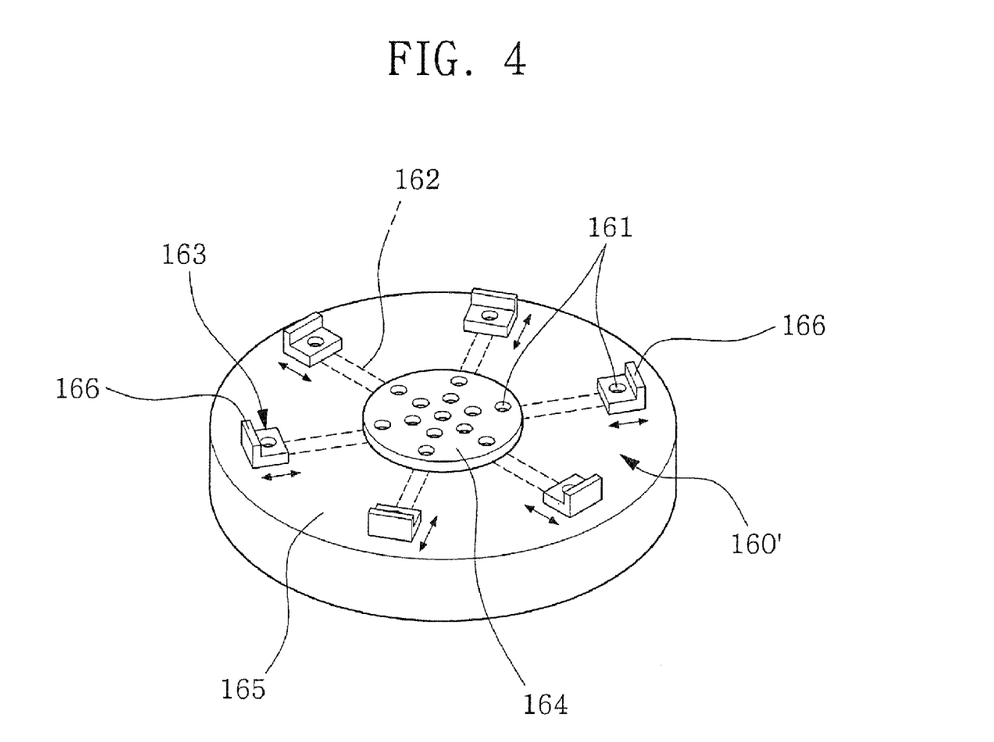
FIG. 4 is a perspective view of a wafer holder in accordance with another exemplary embodiment of the present invention.

Meanwhile, as shown in FIG. 4, a wafer holder 160' may be implemented as another exemplary embodiment in accordance with the present invention. That is, the wafer holder 160' may include a plate 165 having a flat surface, a wafer support block 164 installed at an upper center portion of the plate 165 to support a center part of the wafer W, and a plurality of fitting bars 163 installed at an upper edge of the plate 165, i.e., around the wafer support block 164 and installed to reciprocally move toward and away from the wafer support block 164 to maintain an edge part of the wafer W. At this time, the wafer support block 164 and the plurality of fitting bars may have each at least one vacuum hole 161 for applying a vacuum pressure. Preferably, a plurality of vacuum holes 161 may be formed in the wafer support block 164, more preferably in a radial array. Therefore, the wafer W loaded onto the wafer holder 160 is supported by the wafer support block 164 and the fitting bars 163, and held on upper surfaces of the wafer support block 164 and the fitting bars 163 by vacuum pressure applied through the vacuum holes 161 of the wafer support block 164 and the fitting bars 163. Meanwhile, each of the fitting bars 163 may further have a side support portion 166 for supporting a side surface of the wafer W when the wafer W is mounted onto the fitting bars 163. In this case, the wafer W can be more securely held on the wafer holder 160.

The laser ablation device 110 of FIG. 1 includes a laser irradiation unit 120 for irradiating a laser L, having certain intensity and characteristics, to the wafer W, an optical system 140 for guiding the laser L irradiated from the laser irradiation unit 120 to the specimen collection area and adjusting the intensity and characteristics of the laser L, a monitoring unit 130 for monitoring the specimen collecting unit and the state of the collected specimen, and a laser control unit 115 for adjusting the number, intensity, and characteristics of the laser L irradiated to the specimen collection area using a monitoring value of the monitoring unit 130.

Specifically, the laser irradiation unit 120 includes a laser generator 121 for generating the predetermined laser L to be irradiated to the wafer W, an energy measurement device 122 for measuring intensity of the irradiated laser L, an iris 123 for adjusting an amount of the irradiated laser L, and a shutter 126 for blocking irradiation of the laser L. Therefore, the laser irradiation unit 120 can selectively irradiate a laser having certain intensity and characteristics to the wafer W using the laser generator 121, the energy measurement device 122, the iris 123, the shutter 126, etc.

The optical system 140 is disposed between the laser irradiation unit 120 and the wafer W to guide the laser L irradiated from the laser irradiation unit 120 to the specimen collection area. In addition, the optical system 140 includes a plurality of reflection mirrors 141 and 142 and a plurality of lenses 143, which guide the laser L and adjust the intensity and characteristics of the laser L. Therefore, an operator can move the reflective mirrors 141 and 142 and the lenses 143 manually, or use the laser control unit 115, to guide the irradiated laser L to the specimen collection area and adjust the intensity and characteristics of the irradiated laser L.

The monitoring unit 130 is installed at one side of the optical system 140 to monitor the specimen collecting unit and a state of the collected specimen. The monitoring unit 130 includes a high resolution zoom lens 136 and a CCD camera 137 for precisely monitoring the specimen collection area and the state of the collected specimen, an illuminator 133 for irradiating a predetermined light to the specimen collection area to monitor the specimen collection area, and a prism 135 for refracting the light reflected by the specimen collection area toward the high resolution zoom lens 136. Reference numeral 144 represents a half reflective mirror 144 for reflecting the laser L irradiated from the laser irradiation unit 120 to the specimen collection area and transmitting light reflected by the specimen collection area to the prism 135.

The laser control unit 115 is connected to the laser irradiation unit 120, the optical system 140, and the monitoring unit 130. Therefore, the laser control unit 115 controls the optical system 140 or the laser irradiation unit 120 to adjust the number, intensity, and characteristics of the laser L irradiated to the specimen collection area using a monitoring value of the monitoring unit 130.

Figure 5:
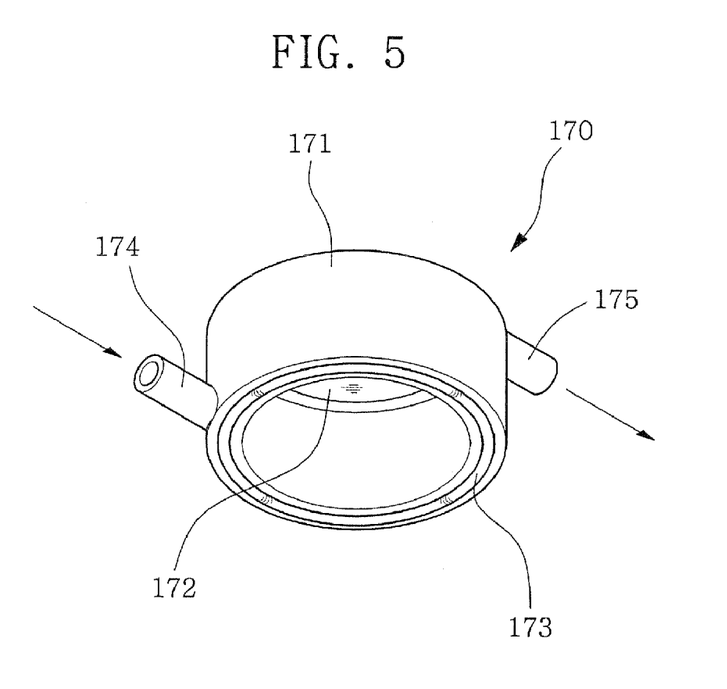
FIG. 5 is a perspective view of the analysis cell shown in FIG. 2.

As shown in FIG. 5, the analysis cell 170 includes a hollow cylindrical cell body 171 having a lower opening in contact with the wafer W and defining the specimen collection area, a window 172 installed at an upper part of the cell body 171 and formed of a transparent material, such as quartz, to transmit the laser L into the cell body 171, a gas inlet part 174 installed at one lower surface of the cell body 171 and supplying a carrier gas into the cell body 171, and a gas discharge part 175 installed at the other upper surface of the cell body 171 to move a specimen collected in the cell body 171 to the analysis device 190 using the carrier gas. A sealing member 174, such as an O-ring, may be installed around a bottom surface of the cell body 171 to isolate the interior of the cell body 171 from the exterior when the cell body 171 is in contact with a surface of the wafer W. In this case, the specimen collection area can be more effectively isolated by the cell body 171 from the exterior.

Figure 6:
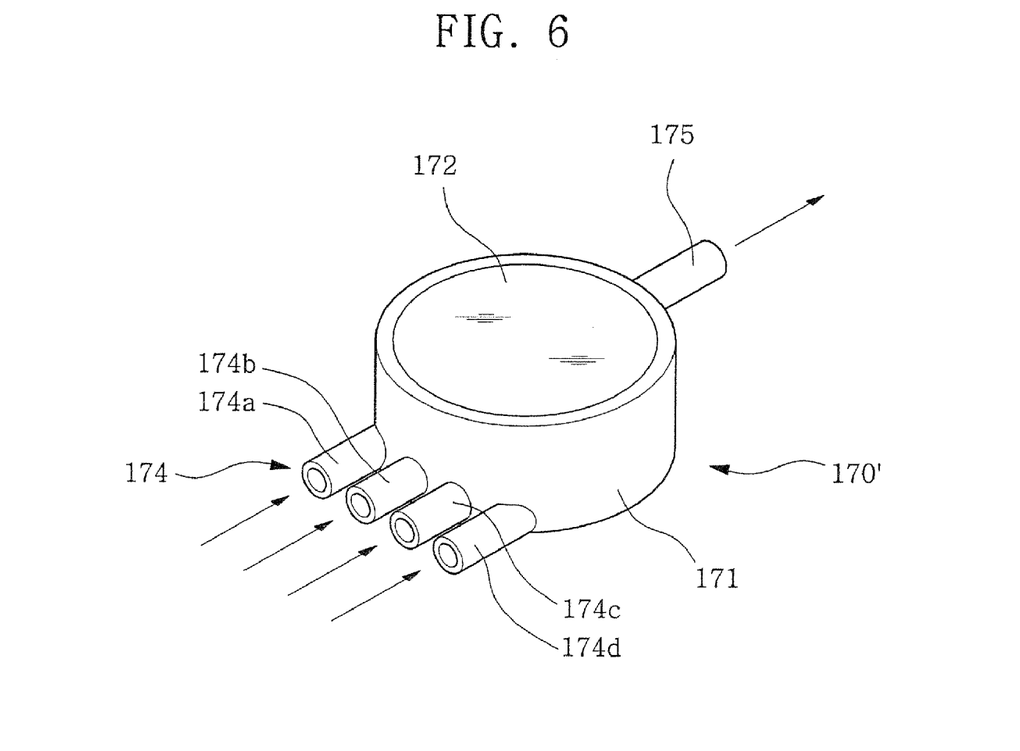
FIG. 6 is a perspective view of an analysis cell in accordance with another exemplary embodiment of the present invention.

Meanwhile, an analysis cell 170' shown in FIG. 6 may be implemented as another embodiment. That is, the analysis cell 170' may include the gas inlet portion 174 formed of a plurality of gas inlet pipes 174a, 174b, 174c and 174d, and a gas discharge part formed of a single gas discharge pipe. In this case, a carrier gas introduced through the plurality of gas inlet pipes 174a, 174b, 174c and 174d can more effectively convey contaminant particulates, i.e., a specimen, ablated in the analysis cell 170 to the analysis device 190. Eventually, when the gas inlet part 174 is formed of the plurality of gas inlet pipes 174a, 174b, 174c and 174d and the gas discharge part 175 is formed of the single gas discharge pipe, it is possible to maximize specimen conveyance efficiency to the analysis device 190.

The analysis device 190 is a device for analyzing contaminants from a specimen using a mass difference between specimens, including a high resolution inductively coupled plasma mass spectroscopy 192, which is widely used in an analysis application, and an analyzer control unit 194 connected thereto. The analysis device 190 is connected to the gas discharge part 175 of the analysis cell 170. Therefore, when the specimen is conveyed to the analysis device 190 through the gas discharge part 175 of the analysis cell 170, the high resolution inductively coupled plasma mass spectroscopy 192 analyzes contaminants from the specimen and transmits analysis data to the analyzer control unit 194. As a result, an operator can rapidly recognize a kind or intensity of contaminants through the analyzer control unit 194.

The specimen conveyance device 180 is connected to the analysis cell 170 to supply a carrier gas into the analysis cell 170 such that the specimen collected from the wafer W is conveyed to the analysis device 190. Specifically, the specimen conveyance device 180 is connected to the gas inlet part 174 of the analysis cell 170 to supply an inert gas as the carrier gas, for example, argon gas. Therefore, the supplied carrier gas conveys a specimen ablated from the wafer W, i.e., the specimen collected from the wafer W by irradiating the laser L to the analysis device 190 through the gas discharge part 175.

The conveyance device 150 is engaged with the wafer holder 160 and the analysis cell 170 to separately or simultaneously move the wafer holder 160 and the analysis cell 170 and to separately or simultaneously adjust the specimen collection area.

Specifically, the moving device 150 includes a holder moving unit 151 engaged with the wafer holder 160 to move the wafer holder 160 in X. Y and Z directions, a cell moving unit 156 engaged with the analysis cell 170 to move the analysis cell 170 in X, Y and Z directions, and a scan unit 154 connected to the holder moving unit 151 and the cell moving unit 156 to simultaneously move the wafer holder 160 and the analysis cell 170.

At this time, as seen in FIG. 2, the holder moving unit 151 may include a first holder moving unit 151a disposed under the wafer holder 160 to reciprocate the wafer holder 160 in a Y-direction, a second holder moving unit 151b connected to the first holder moving unit 15 1a to reciprocate the wafer holder 160 in an X-direction, and a third holder moving unit 151c connected to the second holder moving unit 151b to reciprocate the wafer holder 160 in a Z-direction. The first holder moving unit 151a and the second holder moving unit 151b may use a linear motor, and the third holder moving unit 151c may use a ball screw.

In addition, the cell moving unit 156 may include a cell support frame 155 connected to the cell body 171 of the analysis cell 170, a first cell moving unit 156a connected to the cell support frame 155 to reciprocate the analysis cell 170 in the Y-direction, a second cell moving unit 156b connected to the first cell moving unit 156a to reciprocate the analysis cell in the X-direction, and a third cell moving unit 156c connected to the second cell moving unit 156b to reciprocate the analysis cell 170 in the Z-direction. The first cell moving unit 156a and the second cell moving unit 156b may use a linear motor, and the third cell moving unit 156c may use a ball screw.

Meanwhile, the scan unit 154 is disposed under the holder moving unit 151 and the cell moving unit 156 to be connected to the holder moving unit 151 and the cell moving unit 156, and functions to simultaneously move the wafer holder 160 and the analysis cell 170 in the X and Y directions. At this time, the scan unit 154 may use a linear motor.

Hereinafter, a method of analyzing contaminants on a wafer in accordance with an exemplary embodiment of the present invention will be described in detail with reference to FIG. 7.

Figure 7:
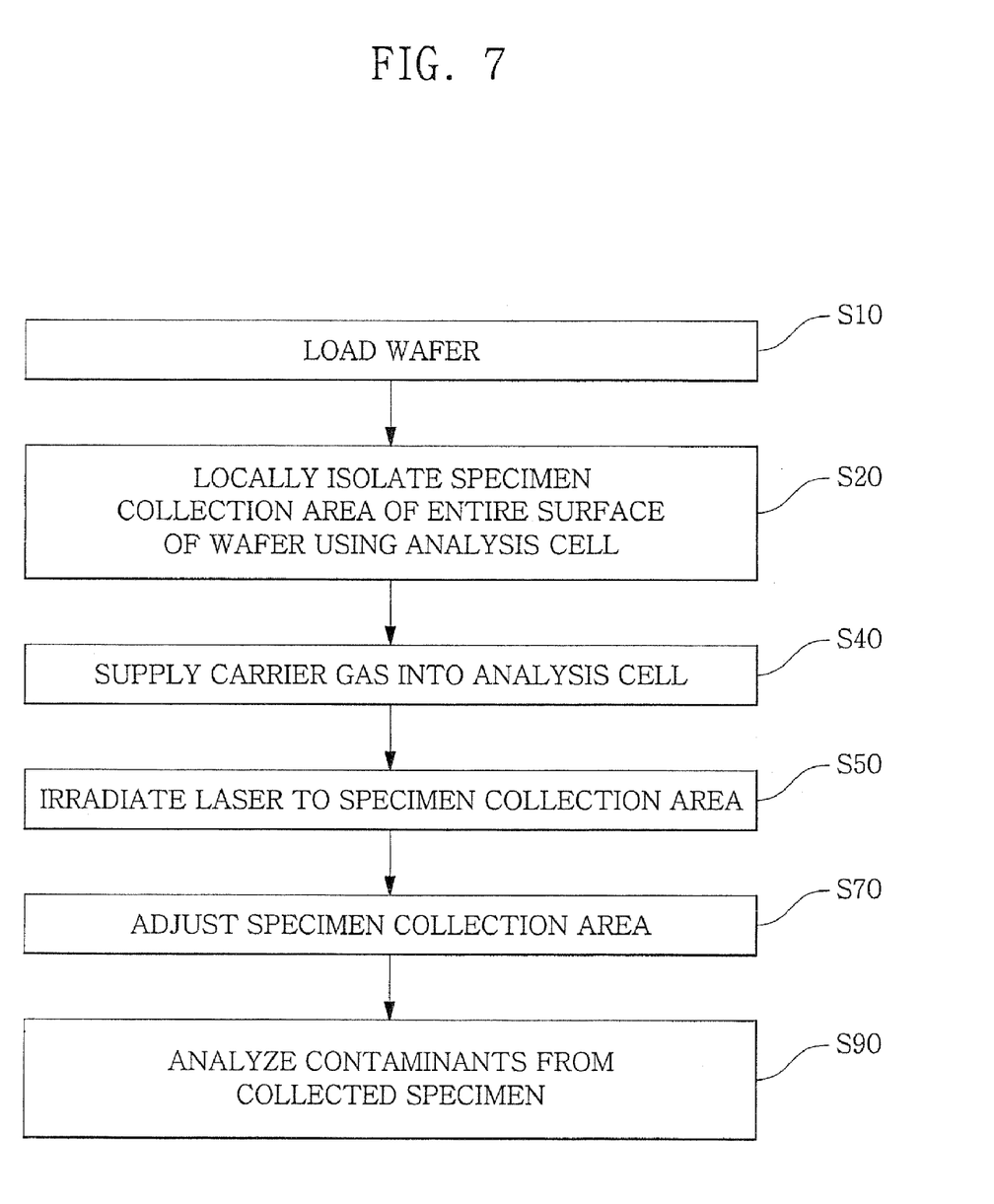
FIG. 7 is a flowchart showing a method of analyzing contaminants on a wafer in accordance with an exemplary embodiment of the present invention.

FIG. 7 is a flowchart showing a method of analyzing contaminants on a wafer in accordance with an exemplary embodiment of the present invention.

First, when a wafer W is provided to analyze contaminants thereon, an operator manually loads the wafer W onto an upper surface of a wafer holder 160 (S10). At this time, the wafer W may be loaded by a wafer conveyance robot.

Then, when the wafer W is loaded onto the wafer holder 160, a central control unit (not shown) entirely controls a wafer contaminant analysis apparatus 100 according to a preset program to provide a predetermined vacuum pressure to vacuum holes 161 of the wafer holder 160 and simultaneously analyzes contaminants on the loaded wafer W. Meanwhile, the wafer W loaded onto the wafer holder 160 is held on an upper surface of the wafer holder 160 by the vacuum pressure provided onto the vacuum holes 161.

Next, when the wafer W is held on the wafer holder 160, a holder moving unit 151 of a moving device 150 moves the wafer holder 160 to position a specimen collection area of the entire surface of the wafer W at a position on which the laser L is irradiated. Therefore, the specimen collection area of the wafer W is disposed at a position on which a laser is to be irradiated according to movement of the wafer holder 160.

Following this, when the specimen collection area of the wafer W is located at the position on which the laser L is irradiated, a cell moving unit 156 of the moving device 150 moves an analysis cell 170 onto the wafer W and then adheres the analysis cell 170 to the specimen collection area of the wafer W, thereby locally isolating the specimen collection area of the wafer W from an exterior (S20).

Then, when the specimen collection area of the wafer W is isolated from the exterior by the analysis cell 170, a specimen conveyance device 180 supplies a carrier gas such as argon gas into the analysis cell so that contaminant particulates ablated in the analysis cell 170, i.e., a specimen, is conveyed into an analysis device 190 (S40).

Next, a laser ablation device 110 selectively irradiates a predetermined intensity and characteristics of laser L to the specimen collection area of the wafer W isolated from the exterior by the analysis cell 170 at predetermined time intervals (S50). Therefore, contaminant particulates, i.e., specimens, are ablated in the analysis cell 170 by irradiating the laser L, and the ablated specimens are conveyed to the analysis device 190 by the carrier gas. Then, the analysis device 190 analyzes the specimen conveyed to the analysis device 190 to determine the kind and level of contamination of the wafer W (S90).

Meanwhile, the moving device 150 can simultaneously move the wafer holder 160 and the analysis cell 170 to a predetermined distance while the laser 1, is irradiated using a scan unit 154 such that the laser L is irradiated onto the entire specimen collection area of the wafer W isolated by the analysis cell 170, rather than a portion in the analysis cell 170 (S70). That is, the scan unit 154 of the moving device 150 can adjust the specimen collection area in which a specimen is collected by the laser L. In this case, since the laser L is irradiated onto the entire specimen collection area of the wafer W isolated by the analysis cell 170, the analysis device 190 can analyze the kind and level of the entire contamination of the specimen collection area.

Hereinafter, specific characteristics of an exemplary embodiment in accordance with the present invention will be described with reference to FIGS. 8 to 10.

Figure 8:
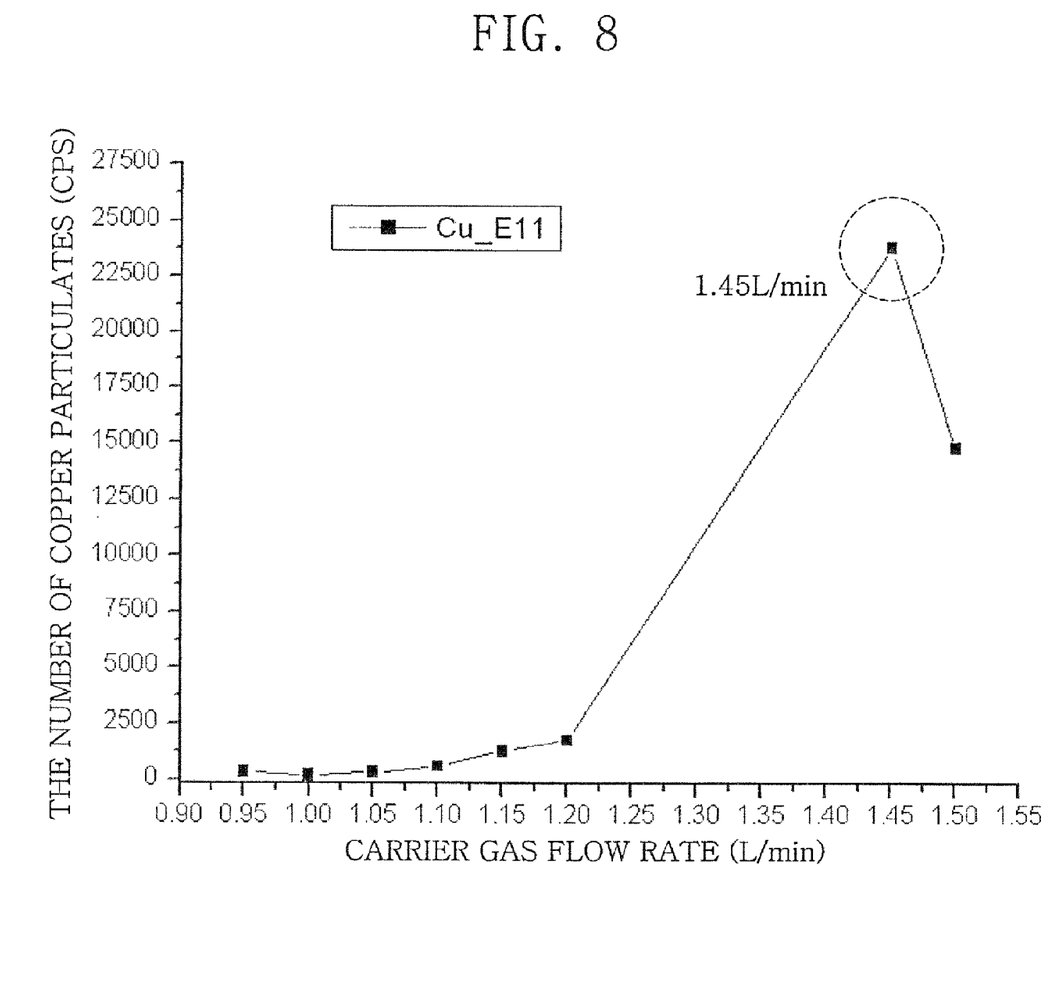
FIG. 8 is a graph showing the relationship between a flow rate of a carrier gas and the number of cooper particulates detected by supplying the carrier gas.

First, when copper material contaminated on a wafer W isolated from the exterior by an analysis cell 170 was to be detected using a wafer contaminant analysis apparatus 100, a carrier gas supply test was performed to determine how much carrier gas should be supplied into the analysis cell 170 in order to obtain an optimal effect, and its result is represented in FIG. 8. The intensity of the laser L irradiated into the analysis cell 170 was 9 mJ, the frequency was 10 Hz, and the defocus was 4000 μm. In addition, the spot size of the laser L was 200 μm, and the shot delay time was 20 sec. As a result, when a copper material on a wafer W is to be detected using the wafer contaminant analysis apparatus 100, an optimal effect can be obtained when the carrier gas is supplied into the analysis cell 170 with the flow rate of 1.45 L/min.

Figure 9A:
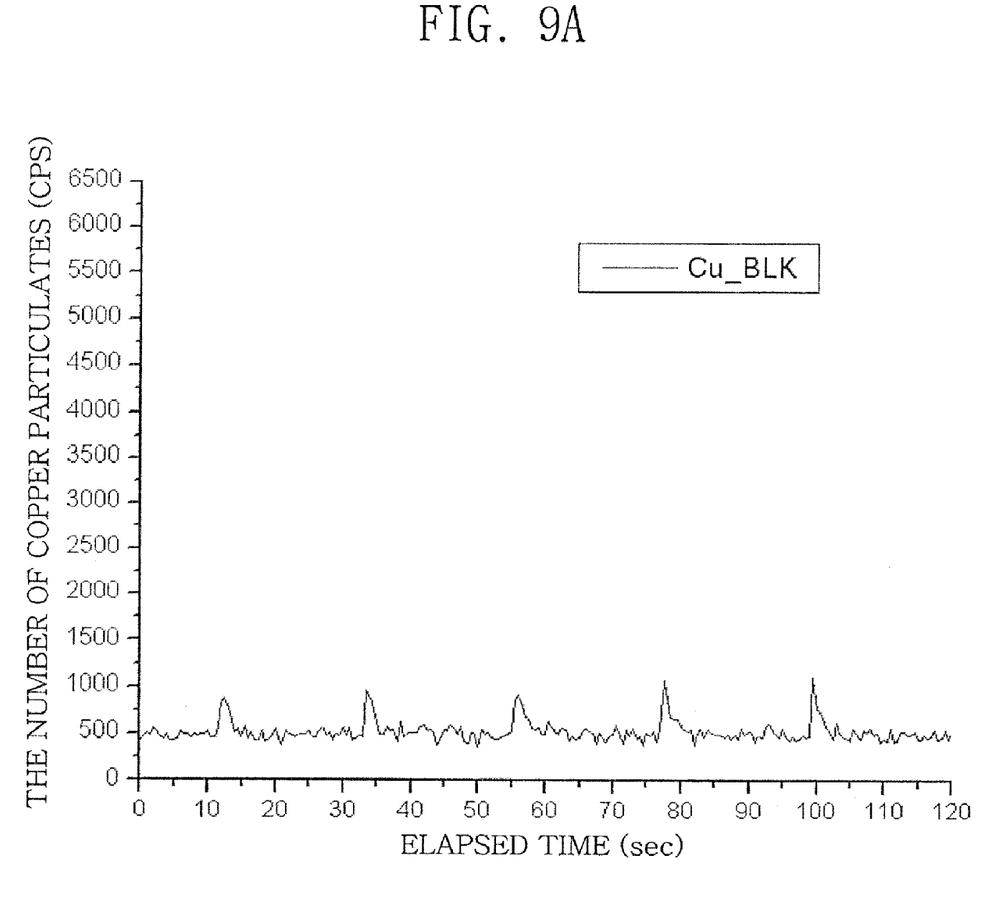
FIG. 9A is a graph showing the relationship between elapsed time and the number of copper particulates detected when detecting a copper material from an uncontaminated wafer using an apparatus for analyzing contaminants on a wafer in accordance with an exemplary embodiment of the present invention.
Figure 9B:
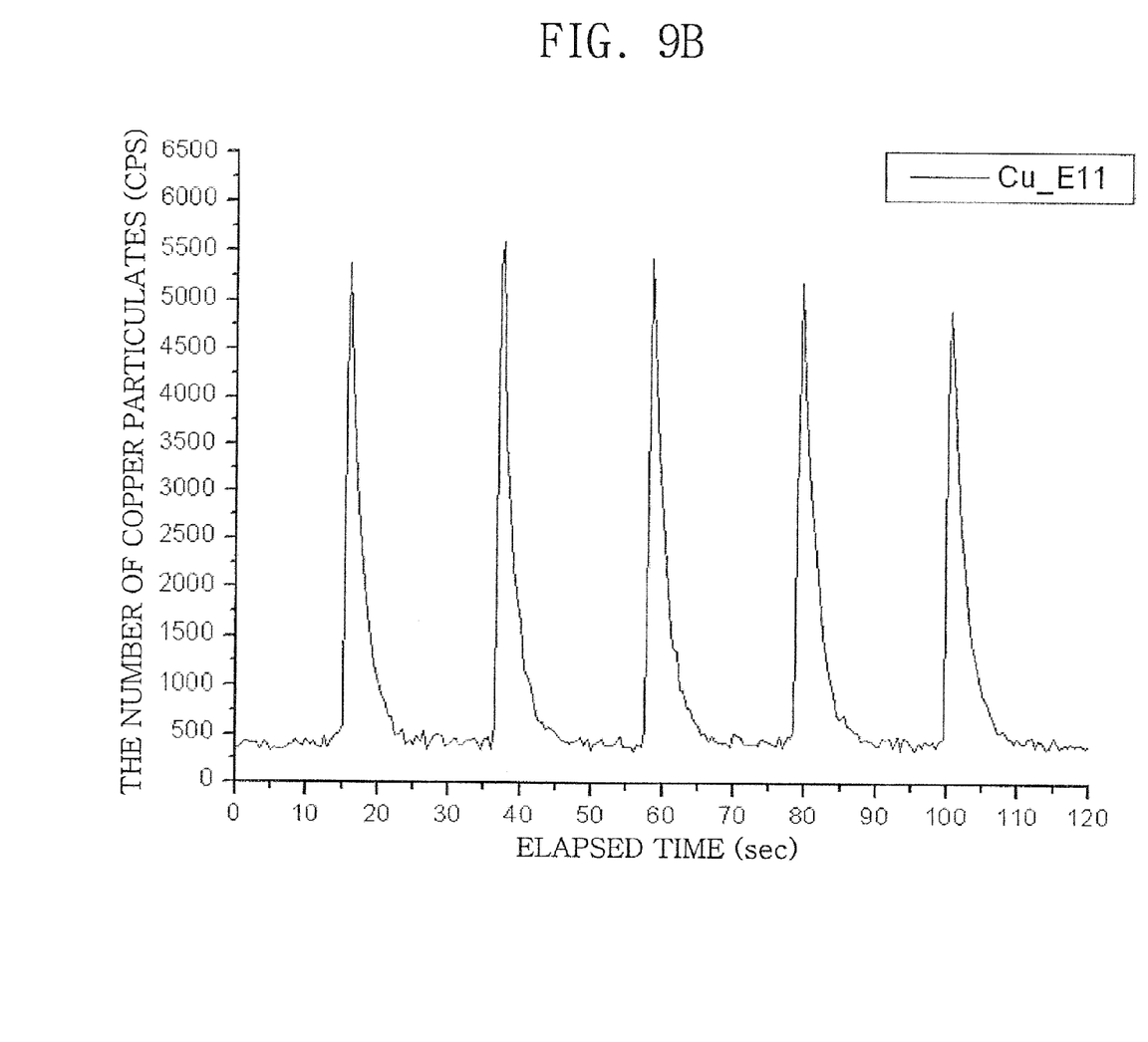
FIG. 9B is a graph showing the relationship between elapsed time and the number of copper particulates detected when detecting a copper material from a copper-contaminated wafer using an apparatus for analyzing contaminants on a wafer in accordance with an exemplary embodiment of the present invention.

Next, when the carrier gas was supplied into the analysis cell 170 with the flow rate of 1.45 L/min together with the above intensity and characteristics of the laser L, in order to determine whether a copper material contaminated on the wafer can be detected effectively, a test for detecting a copper material from a uncontaminated wafer W and a copper-contaminated wafer F using the wafer contaminant analysis apparatus 100 was performed, and its result is represented in FIGS. 9A and 9B. As a result, when the carrier gas was supplied into the analysis cell 170 with the flow rate of 1.45 L/min at the above intensity and characteristics of the laser L, the copper material contaminated on the wafer W can be detected effectively using the wafer contaminant analysis apparatus 100.

Figure 10:
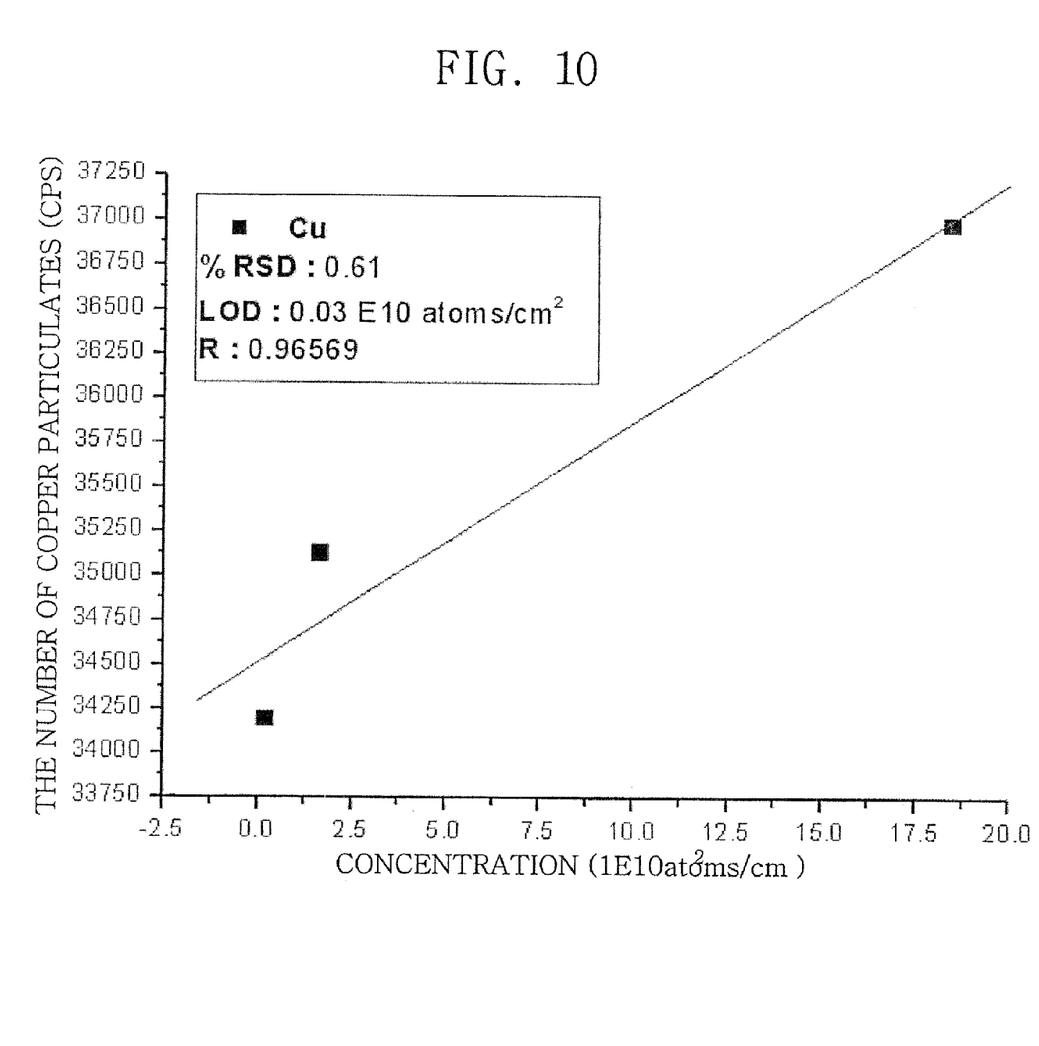
FIG. 10 is a graph showing the relationship between concentration and the number of copper particulates detected when detecting a copper material from various wafers using an apparatus for analyzing contaminants on a wafer in accordance with an exemplary embodiment of the present invention.

Then, a test was conducted for detecting and analyzing a copper material from wafers W having different copper contaminations in order to determine whether the wafer contaminant analysis apparatus 100 can quantitatively analyze various contaminants on the wafer W was performed, and its result is represented in FIG. 10. As a result, when a copper material on the wafer W was detected using the wafer contaminant analysis apparatus 100, as shown in FIG. 10; it will be appreciated that detection values of the various copper contaminants are represented in proportion to concentration of the copper contamination. Therefore, as shown in FIG. 10, it is possible to quantitatively analyze contaminants on the wafer W using the wafer contaminant analysis apparatus in accordance with the present invention.

As can be seen from the foregoing, since an apparatus and method for analyzing contaminants on a wafer can directly detect and analyze contaminants at a wafer level, it is possible to reduce the time taken to manufacture a specimen for analyzing contaminants on a wafer.

In addition, since the apparatus and method for analyzing contaminants on a wafer can directly detect and analysis contaminants at a wafer level, it is possible to prevent contamination generated during the manufacture of the specimen by removing need to manufacture the specimen for analyzing contaminants on a wafer.

Exemplary embodiments of the present invention have been disclosed herein and, although specific terms are employed, they are used and are to be interpreted in a generic and descriptive sense only and not for the purpose of limitation. Accordingly, it will be understood by those of ordinary skill in the art that various changes in form and details may be made without departing from the spirit and scope of the present invention as set forth in the following claims.

What is claimed is:

1. An apparatus for analyzing contaminants on a wafer, comprising:

a wafer holder configured to support a wafer on which contaminants to be analyzed are located;

a laser ablation device that irradiates a wafer, supported by the wafer holder, with laser light to extract a discrete specimen from the wafer;

an analysis cell in which a discrete specimen, extracted from the surface of the wafer by the laser light, is collected; and an analysis device that characterizes particles in a substance, the analysis device being connected to the analysis cell so as to characterize contaminants in the discrete specimen extracted from the wafer.

2. The apparatus according to claim 1, wherein the wafer holder comprises a plate on which the wafer is mounted, the plate having a plurality of vacuum holes for applying a vacuum to the wafer to hold the wafer in place.

3. The apparatus according to claim 2, wherein the vacuum holes are disposed in a radial array extending from the center of the plate.

4. The apparatus according to claim 1, wherein the wafer holder comprises a plate, a wafer support block connected to the plate to support a center portion of the wafer, and a plurality of fitting bars connected to the plate to support an edge part of the wafer.

5. The apparatus according to claim 4, wherein the wafer support block and the plurality of fitting bars include vacuum holes for applying a vacuum to the wafer.

6. The apparatus according to claim 4, wherein each of the fitting bars has a side support portion for supporting a side surface of the wafer when the wafer is mounted on the fitting bars.

7. The apparatus according to claim 6, wherein the fitting bars are connected with respect to the wafer support block such that the fitting bars can move toward or away from the wafer support block.

8. The apparatus according to claim 1, wherein the laser ablation device comprises a laser irradiation unit including a laser, an optical system that guides light emitted by the laser of the laser irradiation unit towards the wafer holder, and a monitoring unit that monitors the extracting of the discrete specimen by the laser light.

9. The apparatus according to claim 8, wherein the laser ablation device further comprises a laser control unit connected to the laser irradiation unit, the optical system, and the monitoring unit, the laser control unit being configured to adjust the laser light used to extract the discrete specimen from the wafer.

10. The apparatus according to claim 1, further comprising a specimen conveyance device including a source of carrier gas, the specimen conveyance device being connected to the analysis cell so that carrier gas is supplied into the analysis cell by the specimen conveyance device, and a gas discharge outlet by which the analysis cell is connected to the analysis device such that carrier gas supplied into the analysis cell by the specimen conveyance device conveys the specimen extracted from the wafer from the analysis cell to the analysis device via the gas discharge outlet.

11. The apparatus according to claim 1, wherein the analysis cell comprises a hollow cell body to contact a wafer supported by the wafer holder and defining an opening through which the discrete specimen is collected, a window in an upper part of the cell body and through which the laser light is transmitted into the cell body, a gas inlet at one side of the cell body and through which carrier gas can be supplied into the cell body, and a gas discharge outlet at another upper part of the cell body and interposed between the cell body and the analysis device such that the specimen collected in the cell body can be conveyed by carrier gas, introduced into the cell body through the gas inlet, to the analysis device.

12. The apparatus according to claim 11, wherein the gas inlet comprises a plurality of pipes, and the gas discharge outlet comprises at least one pipe.

13. The apparatus according to claim 11, wherein the analysis cell further comprises a a seal running along a bottom surface of the cell body so as to isolate the interior of the cell body from the exterior when the bottom surface of the cell body is placed against a wafer supported by the wafer holder.

14. The apparatus according to claim 1, further comprising a moving device engaged with the wafer holder and the analysis cell and operable to move the wafer holder and the analysis cell independently of one another or together.

15. The apparatus according to claim 14, wherein the moving device comprises a holder moving unit engaged with the wafer holder and operable to move the wafer holder in a plurality of directions, a cell moving unit engaged with the analysis cell and operable to move the analysis cell in a plurality of directions, and a scan unit connected to the holder moving unit and the cell moving unit and operable to move the wafer holder and the analysis cell together via the holder and cell moving units.

16. The apparatus according to claim 1, wherein the analysis device comprises a high-resolution inductively coupled plasma mass spectroscope (HR-ICP-MS).

17. A method of analyzing contaminants on a wafer, comprising:
 loading a wafer on a wafer holder;
 isolating a region of one surface of the wafer, as a specimen collection area, using an analysis cell;
 irradiating the isolated specimen collection area with laser light to extract a specimen from the wafer; and
 characterizing contaminants on the wafer by analyzing the specimen extracted from the wafer.

18. The method according to claim 17, further comprising collecting the specimen extracted from the surface of the wafer in the analysis cell, and conveying the collected specimen from the interior of the analysis cell to an analysis device which conducts said analyzing of the specimen.

19. The method according to claim 17, further comprising changing the specimen collection area by changing the position of the wafer holder relative to that of the analysis cell.

20. The method according to claim 17, further comprising scanning the specimen collection area with the laser light by moving the wafer holder and the analysis cell together.

\* \* \* \* \*